(12) United States Patent
Bowsman

(10) Patent No.: US 6,237,770 B1
(45) Date of Patent: *May 29, 2001

(54) CONTAINER WITH REINFORCED TAB

(75) Inventor: Randall J. Bowsman, Walnut, CA (US)

(73) Assignee: Ray Products, Inc., Ontario, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/387,391

(22) Filed: Sep. 2, 1999

Related U.S. Application Data

(63) Continuation of application No. 09/108,272, filed on Jul. 1, 1998, now Pat. No. 5,971,152.

(51) Int. Cl.⁷ ...................................................... A61L 2/00
(52) U.S. Cl. ........................... 206/438; 206/370; 206/447
(58) Field of Search .................................... 206/438, 439, 206/363, 370, 557, 559–565, 447, 520, 223, 568; 422/300, 297, 310; 220/23.89, 23.87, 528, 645, 639, 651, 675; 264/239, 241; 53/432, 433, 467; 312/242, 351

(56) References Cited

U.S. PATENT DOCUMENTS

| 3,314,741 | * | 4/1967 | Litner ................................... 312/242 |
| 3,416,703 | | 12/1968 | Chmielowiec . |
| 4,482,053 | | 11/1984 | Alpern et al. . |
| 4,697,703 | | 10/1987 | Will . |
| 4,750,619 | | 6/1988 | Cohen et al. . |
| 5,266,763 | | 11/1993 | Colombo . |
| 5,375,735 | | 12/1994 | Huvey et al. . |
| 5,393,539 | | 2/1995 | Reskow . |
| 5,441,707 | | 8/1995 | Lewis et al. . |
| 5,971,152 | | 10/1999 | Bowsman . |

* cited by examiner

Primary Examiner—Luan K. Bui
(74) Attorney, Agent, or Firm—Thelen Reid & Priest LLP; David B. Ritchie

(57) ABSTRACT

A package having a container having an inner surface, an outer surface, and a sidewall defining a cavity, with the container having an inner locking tab in the cavity defining a recess in the outer surface of the container, and with a stiffening material being placed in the recess to add strength to the locking tab.

5 Claims, 3 Drawing Sheets

CONTAINER WITH REINFORCED TAB

CROSS REFERENCE TO A RELATED APPLICATION

This application is a continuation of U.S. Pat. application Ser. No. 09/108,272, filed on Jul. 1, 1998, Entitled "CONTAINER WITH REINFORCED TAB" by inventor Randall J. Bowsman, and issued as U.S. Pat. No. 5,971,152 on Oct. 26, 1999.

BACKGROUND OF THE INVENTION

1. Field of the Invention

The present invention relates to packages, and more particularly to sterile packages having a plurality of sterile articles therein. Still more particularly, it relates to the carriage of products within such packages.

2. The Background Art

Sterile packages for retaining a plurality of sterile articles are known. Typically, such packages have a tray with recesses, with the sterile articles being received in the recesses. The recesses are commonly covered with a cover permeable to the passage of a sterilization gas and impermeable to the passage of bacteria. The tray and articles are rendered sterile by passing the sterilization gas through the cover and onto the articles and tray. The covered trays may then be stored and transported while maintaining the sterile barrier in the tray. At the time of a medical procedure, the cover is removed by operating personnel to expose the sterile articles for use in the procedure. For larger sterile articles, a large container may be used with a tray retaining the sterile articles being received in a cavity of the container.

In a suitable form, such containers may be vacuum formed, by a process in which a plastic sheet is clamped to a frame, and the sheet is heated and drawn down into a mold by a vacuum. Since the entire package is preferably disposable, it is desirable to minimize the thickness of its walls in order to reduce the cost and bulk of the container. This also aids in allowing the sheet to conform to the mold. However, the vacuum formed container may have regions of weakness due to a reduced thickness of the wall induced by the vacuum forming process. In this case, the region of weakness may rupture or tear, thus exposing the sterile articles to the atmosphere which may cause contamination of the tray unknown to the attending operating personnel, with possible deleterious results to the patient.

In one form, the plastic sheet and corresponding container walls may be made thicker, but, in that case all of the walls in the container will also be thicker which is actually unnecessary, adding to the cost of the sterile container, as well as its bulk, and complicating the vacuum forming process. Hence, it is desirable to provide a sterile container at minimum cost and thickness and maximum strength to prevent contamination of the sterile articles which are used in the procedure.

BRIEF DESCRIPTION OF THE INVENTION

In accordance with the present invention, a package includes a container having an inner surface, an outer surface, and a sidewall defining a cavity having an opening to the exterior of the container. The container has an inner support tab in the cavity defining a recess in the outer surface of the container. A stiffening material is placed in the recess to add strength to the support locking tab. The support tab or tabs support an article or product disposed in the container. In a preferred form, the package of which the container is a part is sterile, and retains sterile articles for use in a medical procedure. Such sterility is achieved by the inclusion of a removable seal member covering and sealing the opening in the container. In a preferred form, the seal member is permeable to a sterilization gas and impermeable to the passage of bacteria.

FEATURES AND ADVANTAGES OF THE INVENTION

A principle feature of the present invention is the provision of an improved sterile package.

A feature and advantage of the invention is that outer recesses of the locking or support tabs are filled with a stiffening material.

Another feature and advantage of the invention is that the stiffened locking or support tabs are much more resistent to tear or rupture of the container in the region of the locking or support tabs than when they are left unstiffened.

Yet another feature and advantage of the invention is that the stiffened locking or support tabs reduce the likelihood that the sterile barrier of the package will be compromised during normal handling.

A further feature and advantage of the invention is that the walls of the container may be made of a reduced thickness to minimize the cost and bulk of the package without thereby compromising the strength and survivability of the package.

These and many other features and advantages of the present invention will become apparent to those of ordinary skill in the art from a consideration of the drawings and ensuing description of the invention.

DETAILED DESCRIPTION OF A PREFERRED EMBODIMENT

Figure 1:
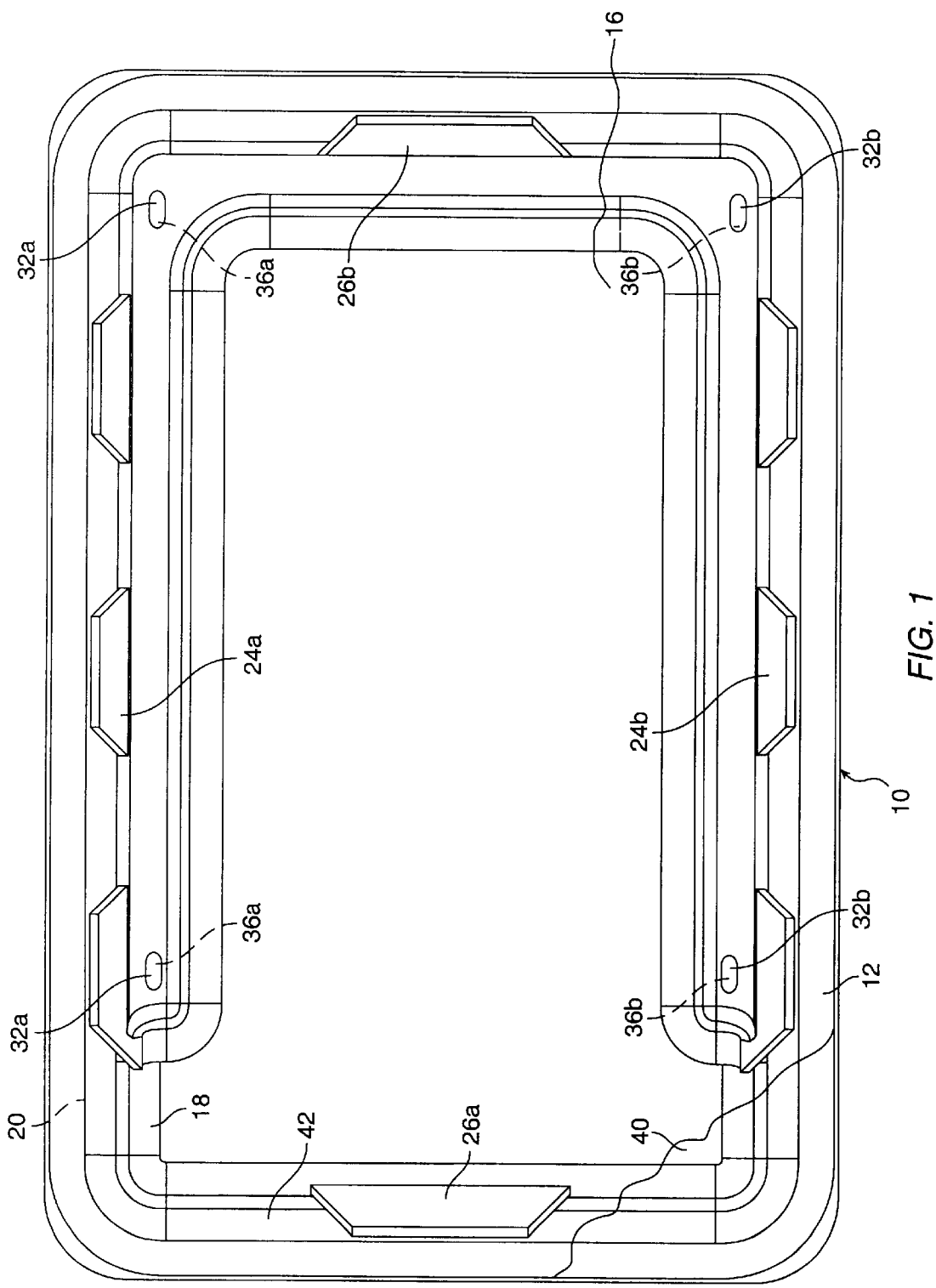
FIG. 1 is a plan view of a container in accordance with a presently preferred embodiment of the present invention.

Those of ordinary skill in the art will realize that the following description of the present invention is illustrative only and not in any way limiting. Other embodiments of the invention will readily suggest themselves to such skilled persons.

Referring now to FIGS. 1, 2, 3, 4 and 5, there is shown a package generally designated 10 having a container 12 and a tray 14 which is received in a cavity 16 of the container 12. Although it is preferred that the package 10 be rendered sterile for use in medical procedures, it is understood that the package need not be sterile for other uses.

Figure 2:
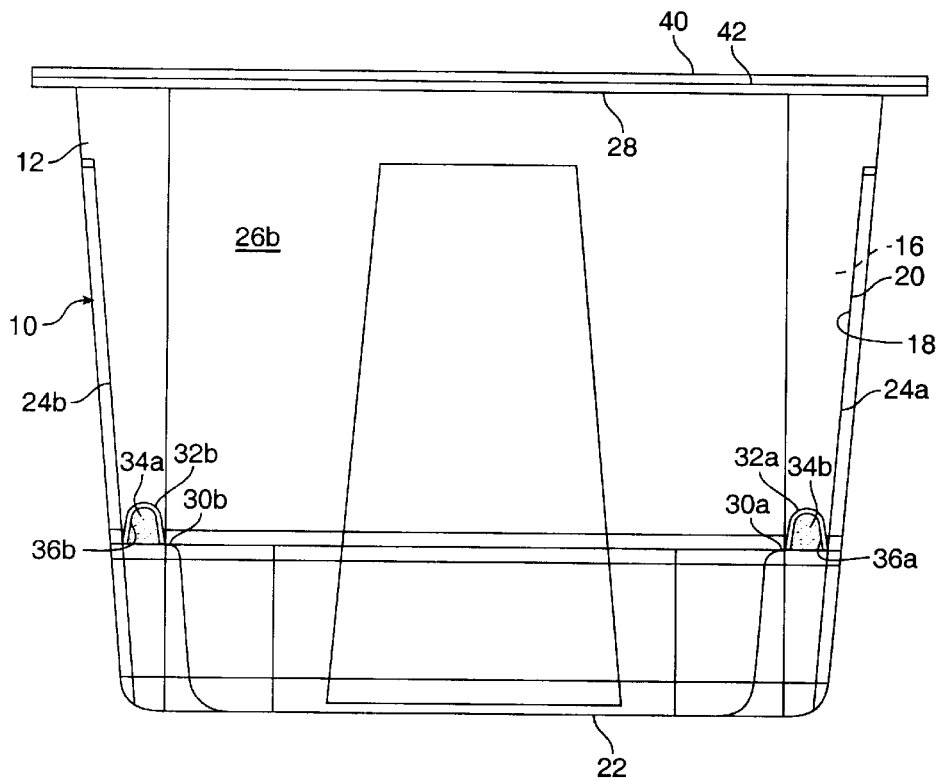
FIG. 2 is an end elevational view of the container of FIG. 1.
Figure 5:
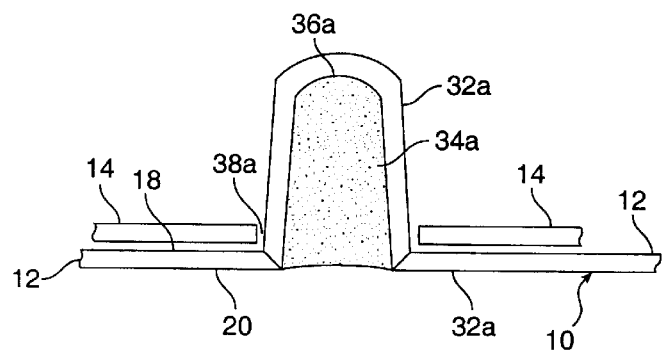
FIG. 5 is a fragmentary sectional view showing a filled locking or support tab of the container of FIGS. 1 and 2 and corresponding opening or slot of the tray of FIGS. 3 and 4 in accordance with a presently preferred embodiment of the present invention.

With reference to FIGS. 1, 2, and 5, the container 12 is preferably vacuum formed from a thermoplastic material, such as styrene with about 5–7% rubber. Those of ordinary skill in the art will realize that other materials can readily be substituted. The container 12 has an inner surface 18, an outer surface 20, and an inner bottom wall 22. The container 12 in accordance with this preferred embodiment has a pair of opposed sidewalls 24a and 24b connected to the inner bottom wall 22, and a pair of opposed end walls 26a and 26b connected to said inner wall 22 and sidewalls 24a and 24b to define the inner sterile cavity 16 communicating with an outer opening 28 in the container 12.

The container sidewalls 24a and 24b have a pair of corresponding opposed inner ledges 30a and 30b spaced from the inner bottom wall 22, and a pair of upstanding locking or support tabs 32a and 32b on the ledges 30a and 30b, respectively, and projecting into the cavity 16, as shown in FIG. 2. The locking tabs 32a and 32b naturally correspond with a plurality of recesses 34a and 34b in the outer surface 20 of the ledges 30a and 30b. The recesses 34a and 34b are filled in accordance with the invention with a stiffening agent or material 36a and 36b, such as a curable epoxy filler or other hardenable material which may be injected into the recessed 34a and 34b. This is done in order to enhance the rigidity and strength of the locking tabs 32a and 32b to prevent rupture or tearing of the locking tabs 32a and 32b, resulting in loss of sterility in the inside of the package 10 and container 12.

The introduction of the stiffening agent 36a and 36b to the outside of container 12 avoids the possibility of locking contaminants into a matrix within the sterile container. Any contaminants associated with the stiffening agent are isolated from the contents of the package 10 by the wall of the container at the recess.

Figure 4:
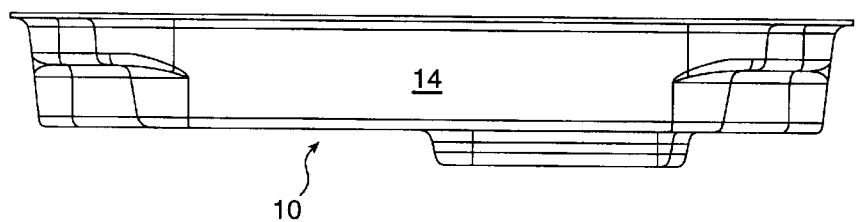
FIG. 4 is an end elevational view of the tray of FIG. 3.
Figure 3:
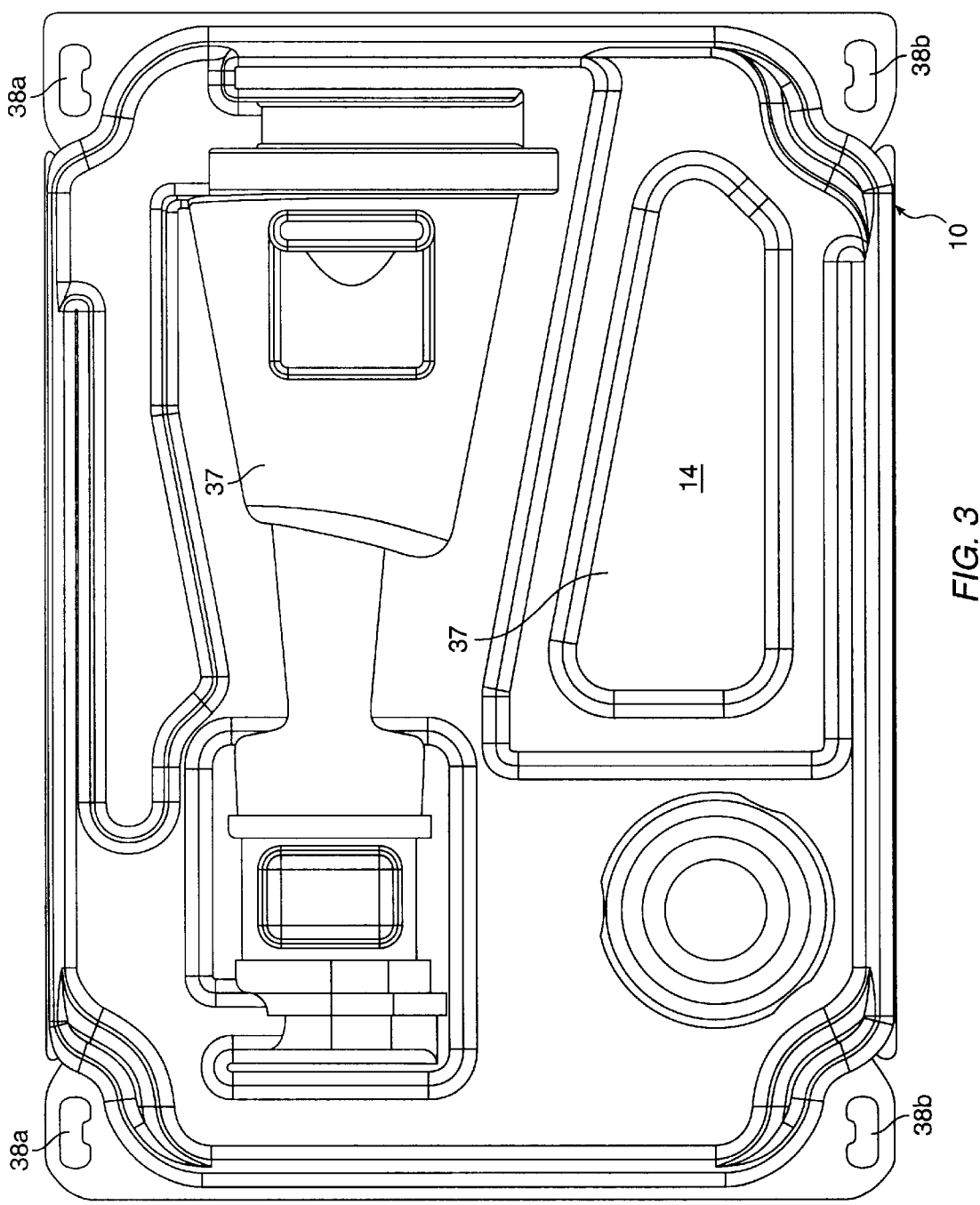
FIG. 3 is a plan view of a tray for use in a container in accordance with a presently preferred embodiment of the present invention.

With reference to FIGS. 3, 4, and 5, the sterile tray 14 is removably received in the cavity 16 of the container 12, and has a plurality of recesses 37 to retain sterile articles therein, such as parts used in a blood reoxygenator and purifier. The tray 14 has a plurality of openings 38a and 38b which register and engage with the locking tabs 32a and 32b when the tray 14 is placed on the ledges 30a and 30b in the cavity 16 to receive the locking tabs 32a and 32b and releasably retain the tray 14 at a desired position in the cavity 16. The tray 14 is spaced from the inner bottom wall 22 in order to provide room for a sterile component intermediate the tray 14 and inner wall 22, such as for the blood reoxygenator and purifier and tubing associated therewith. The tray 14 may be constructed from the same vacuum formed material as the container 12.

As shown in FIGS. 1 and 2, the package 10 has a cover 40 releasably sealed to an outer outwardly directed flange 42 of the container 12, with the flange 42 extending peripherally around the container 12. The cover 40 is permeable to the passage of a sterilizing gas and is impermeable to the passage of bacteria. The cover 40 may be constructed from a sheet termed TYVEK®, a product of E. I. Dupont deNemours, Wilmington, Del. Those of ordinary skill in the art will readily realize that other materials could also be used.

Thus, the articles are placed in the recesses 37 of the tray 14, and the component is placed on the inner bottom wall 22. The tray 14 is then placed on the ledges 30a and 30b of the container 12. Next, the cover 40 is sealed to the container flange 42, and the inside of the container 12 is sterilized by passing a sterilization gas, such as ethylene oxide, through the cover 40 in order to render the articles and component sterile, in addition to the container cavity 16 and tray 14. At the time of use, the cover 40 is removed from the container 12 in order to expose the articles and component in a sterile condition for use in a medical procedure.

Thus, in accordance with the present invention, the locking tabs 32a and 32b are strengthened in order to prevent rupture or tearing of the locking tabs 32a and 32b which may cause contamination to the inside of the package 10. As a result, a thinner wall may be used for the container 12 without jeopardizing the sterile barrier of the package 10 in order to reduce the cost and bulk of the package 10.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims. It is particularly to be understood that the present invention is applicable to non-sterile applications, and is useful wherever a strengthened support tab or support member is needed in a vacuum formed plastic item.

What is claimed is:

1. A package, comprising:

a container of a first material, said container defining a first cavity, said container having an aperture into said first cavity, said aperture being sealable and openable;

a tray receivable into said first cavity;

a ledge on said container, said ledge supporting said tray; and a protrusion on said ledge, said protrusion restricting motion of said tray on said ledge, said protrusion defining a second cavity protruding into said first cavity, said second cavity containing a second material to enhance rigidity of said protrusion.

2. The package of claim 1 wherein said container is formed from a thermoplastic material.

3. The package of claim 1 wherein said second material in said second cavity is curable.

4. The package of claim 1 wherein said second material in said second cavity is epoxy.

5. A package, comprising:

a container having a first surface and a second surface, said first surface defining a cavity, said cavity having an aperture for receiving a tray;

a ledge on said first surface and within said cavity, said ledge supporting said tray;

a locking tab on said ledge protruding into said cavity, said locking tab restricting movement of said tray on said ledge, said locking tab defining a recess; and a stiffening material within said recess for strengthening said locking tab.

* * * * *